US011978534B1

(12) United States Patent
Woodbury

(10) Patent No.: US 11,978,534 B1
(45) Date of Patent: May 7, 2024

(54) PREDICTION OF BINDING FROM BINDING DATA IN PEPTIDE AND OTHER ARRAYS

(71) Applicant: ARIZONA BOARD OF REGENTS ON BEHALF OF ARIZONA STATE UNIVERSITY, Scottsdale, AZ (US)

(72) Inventor: Neal Woodbury, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 1356 days.

(21) Appl. No.: 16/029,965

(22) Filed: Jul. 9, 2018

Related U.S. Application Data

(60) Provisional application No. 62/529,861, filed on Jul. 7, 2017.

(51) Int. Cl.
*G16B 40/00* (2019.01)
*G01N 33/68* (2006.01)
*G16B 5/00* (2019.01)

(52) U.S. Cl.
CPC ......... *G16B 40/00* (2019.02); *G01N 33/6845* (2013.01); *G01N 33/6878* (2013.01); *G16B 5/00* (2019.02)

(58) Field of Classification Search
CPC ...... G16B 40/00; G16B 5/00; G01N 33/6845; G01N 33/6878
USPC .......................................................... 703/12
See application file for complete search history.

(56) References Cited

U.S. PATENT DOCUMENTS

| 9,970,932 | B2 | 5/2018 | Woodbury |
| 10,006,919 | B2 | 6/2018 | Woodbury |
| 10,046,293 | B2 | 8/2018 | Woodbury |
| 10,427,125 | B2 | 10/2019 | Woodbury |
| 2008/0188618 | A1 | 8/2008 | Greving |
| 2010/0056392 | A1 | 3/2010 | Greving |
| 2011/0201511 | A1 | 8/2011 | Hayes |
| 2012/0094271 | A1 | 4/2012 | Fu |

(Continued)

FOREIGN PATENT DOCUMENTS

| WO | 2005108992 A1 | 11/2005 |
| WO | 2006138479 A2 | 12/2006 |

(Continued)

OTHER PUBLICATIONS

Phillip Stafford, Zbigniew Cichacz, Neal W. Woodbury, and Stephen Albert Johnston: ("Immunosignature system for diagnosis of cancer", PNAS | Published online Jul. 14, 2014) (Year: 2014).*

(Continued)

*Primary Examiner* — Russell S Negin
*Assistant Examiner* — Guozhen Liu
(74) *Attorney, Agent, or Firm* — Quarles & Brady, LLP

(57) ABSTRACT

Systems, devices and methods for predicting binding on an array such as a peptide array. Certain methods utilize a peptide array having a plurality of peptides with one or more defined parameters and contacting the peptide array with a training sample containing one or more molecules of interest. Interactions between the plurality of peptides and the one or more molecules of interest are processed according to a data fitting model, which model is then is applied to interactions between the plurality of peptides and a test sample to predict binding associated with the one or more molecules of interest.

14 Claims, 20 Drawing Sheets

(56) References Cited

U.S. PATENT DOCUMENTS

| | | |
|---|---|---|
| 2017/0106344 A1 | 4/2017 | Woodbury |
| 2018/0259510 A1 | 9/2018 | Woodbury |
| 2018/0275136 A1 | 9/2018 | Woodbury |
| 2019/0034580 A1 | 1/2019 | Woodbury |
| 2019/0050524 A1 | 2/2019 | Woodbury |
| 2019/0064177 A1 | 2/2019 | Woodbury |

FOREIGN PATENT DOCUMENTS

| | | |
|---|---|---|
| WO | 2007109067 A2 | 9/2007 |
| WO | 2008091378 A3 | 7/2008 |
| WO | 2009009028 A1 | 1/2009 |
| WO | 2009067657 A2 | 5/2009 |
| WO | 2010027642 A2 | 3/2010 |
| WO | 2010028214 A2 | 3/2010 |
| WO | 2012154594 A1 | 11/2012 |
| WO | 2014062981 A1 | 4/2014 |
| WO | 2014144383 A1 | 9/2014 |
| WO | 2014145123 A2 | 9/2014 |
| WO | 2018170003 A1 | 9/2018 |
| WO | 2018187687 A1 | 10/2018 |
| WO | 2019152943 A1 | 8/2019 |

OTHER PUBLICATIONS

Andrew L. Ferguson, Emilia Falkowska, Laura M. Walker, Michael S. Seaman, Dennis R. Burton, Arup K. Chakraborty: Computational Prediction of Broadly Neutralizing HIV-1 Antibody Epitopes from Neutralization Activity Data, Plos One, 8(12): e80562. Dec. 2, 2013 (Year: 2013).*

Björn Forsström, Barbara Bisławska Axnäs, Klaus-Peter Stengele, Jochen Bühler et al: Proteome-wide Epitope Mapping of Antibodies Using Ultra-dense Peptide Arrays, Molecular & Cellular Proteomics, vol. 13, Issue 6, p. 1585-1597, Jun. 1, 2014 (Year: 2014).*

Sykes, Kathryn F., Joseph B. Legutki, and Phillip Stafford. "Immunosignaturing: a critical review." Trends in biotechnology 31.1 (2013): 45-51. (Year: 2013).*

Legutki, Joseph Barten, et al. "Scalable high-density peptide arrays for comprehensive health monitoring." Nature communications 5.1 (2014): 4785. (Year: 2014).*

Hecker, Michael, et al. "Computational analysis of high-density peptide microarray data with application from systemic sclerosis to multiple sclerosis." Autoimmunity reviews 11.3 (2012): 180-190. (Year: 2012).*

Hecker, Michael, et al. "High-density peptide microarray analysis of IgG autoantibody reactivities in serum and cerebrospinal fluid of multiple sclerosis patients." Molecular & cellular proteomics 15.4 (2016): 1360-1380. (Year: 2016).*

Andresen, Heiko, and Carsten Grotzinger. "Deciphering the antibodyome-peptide arrays for serum antibody biomarker diagnostics." Current Proteomics 6.1 (2009): 1-12. (Year: 2009).*

Forsström, Björn, et al. "Proteome-wide epitope mapping of antibodies using ultra-dense peptide arrays." Molecular & Cellular Proteomics 13.6 (2014): 1585-1597. (Year: 2014).*

Gozalbes, R. et al. "Small molecule databases and chemical descriptors useful in chemoinformatics: an overview." Combinatorial chemistry & high throughput screening 14.6 (2011): 548-558.

Sandberg, M., et al. "New chemical descriptors relevant for the design of biologically active peptides. A multivariate characterization of 87 amino acids." Journal of medicinal chemistry 41.14 (1998): 2481-2491.

U.S. Appl. No. 16/489,099.
U.S. Appl. No. 16/603,338.

* cited by examiner

701

| AEEL | 1 | 2 | 3 | 4 |
|---|---|---|---|---|
| N | 0 | 0 | 0 | 0 |
| E | 0 | 1 | 1 | 0 |
| A | 1 | 0 | 0 | 0 |
| L | 0 | 0 | 0 | 1 |

702

| LNEA | 1 | 2 | 3 | 4 |
|---|---|---|---|---|
| N | 0 | 1 | 0 | 0 |
| E | 0 | 0 | 1 | 0 |
| A | 0 | 0 | 0 | 1 |
| L | 1 | 0 | 0 | 0 |

703

| ENNA | 1 | 2 | 3 | 4 |
|---|---|---|---|---|
| N | 0 | 1 | 1 | 0 |
| E | 1 | 0 | 0 | 0 |
| A | 0 | 0 | 0 | 1 |
| L | 0 | 0 | 0 | 0 |

704

| COEF | 1 | 2 | 3 | 4 |
|---|---|---|---|---|
| N | .45 | -.22 | .9 | .03 |
| E | -.55 | 1.2 | .08 | .88 |
| A | -.32 | -.65 | 1.5 | .11 |
| L | .47 | .29 | -1.1 | .21 |

FIG. 5

Pearson Correlation Between the Fit and the Measured Values

Concentrations (pM)

| 4C1 | correlation | p53Ab1 | DM1A |
|---|---|---|---|
| 8000.00 | | 0.00 | 0.00 |
| | 1.00 | | |
| 2666.67 | | 98.77 | 0.00 |
| | 0.94 | | |
| 888.89 | | 0.01 | 0.00 |
| | 0.80 | | |
| 296.30 | | 0.00 | 0.00 |
| | 0.65 | | |
| 98.77 | | 10.97 | 0.00 |
| | 0.53 | | |
| 32.92 | | 8000.00 | 0.00 |
| | 0.99 | | |
| 10.97 | | 1.22 | 0.00 |
| | 0.29 | | |
| 3.66 | | 0.00 | 0.01 |
| | 0.30 | | |
| 1.22 | | 296.30 | 0.01 |
| | 0.68 | | |
| 0.41 | | 0.00 | 0.04 |
| | 0.17 | | |
| 0.14 | | 2666.67 | 0.14 |
| | 0.79 | | |
| 0.04 | | 0.00 | 0.41 |
| | 0.26 | | |
| 0.01 | | 0.04 | 1.22 |
| | 0.13 | | |
| 0.01 | | 0.00 | 3.66 |
| | 0.28 | | |
| 0.00 | | 3.66 | 10.97 |
| | 0.27 | | |
| 0.00 | | 0.00 | 32.92 |
| | 0.44 | | |
| 0.00 | | 0.14 | 98.77 |
| | 0.62 | | |
| 0.00 | | 888.89 | 296.30 |
| | 0.72 | | |
| 0.00 | | 32.92 | 888.89 |
| | 0.85 | | |
| 0.00 | | 0.01 | 2666.67 |
| | 0.94 | | |
| 0.00 | | 0.41 | 8000.00 |
| | 1.00 | | |
| 0.00 | | 0.00 | 0.00 |
| | N/A | | |

FIG. 7 mAb 4C1: Epitope Prediction using Mono-Peptide fit mAb 4C1: Epitope Prediction using Di-Peptide fit mAb 4C1: Epitope Prediction using Tri-Peptide fit mAb p53Ab1: Epitope Prediction using Tri-Peptide fit mAb DM1A: Epitope Prediction using Tri-Peptide fit

Scatter Plot of Predicted Data vs. Observed using Test Peptides

Correlation (Model vs. Data) w/ Increasing # of Peptides fitting one position at a time

PREDICTION OF BINDING FROM BINDING DATA IN PEPTIDE AND OTHER ARRAYS

CROSS-REFERENCE TO RELATED APPLICATION

This application claims the benefit of U.S. Provisional Patent Application No. 62/529,861, filed on Jul. 7, 2017, the disclosure of which is incorporated by reference herein in its entirety.

STATEMENT AS TO FEDERALLY SPONSORED RESEARCH

This invention was made with the support of the United States government under Contract number 1243082 by National Science Foundation. The government has certain rights in the invention.

BACKGROUND OF THE INVENTION

Molecular arrays are useful tools for diagnosing various types of diseases. The manufacture of molecular arrays can be sensitive to a large number of distinct parameters, including the nature of biochemical molecules present in the array. An efficient way to characterize the chemical structures of arrays in terms of their binding properties is useful in optimizing array performance and manufacturing yield of molecular arrays that consistently have high quality.

SUMMARY OF THE INVENTION

Methods and simulation tools for new platforms establishment are disclosed herein. Embodiments herein are based on binding of antibodies, for example, in a fluid sample to peptides on an array. In principle, there are a set of fixed chemical structures interacting with the complex biological or chemical sample, followed by measurements being made from each of the fixed chemical structures or some subset of those structures. On the other hand, creation of an array varies by a number of factors; when being optimized, simulations can allow an array designer to foresee various features of the array in order to optimize assay development. This includes optimization of feature characteristics necessary to increase sensitivity and specificity of the array platform. In addition, chemically based simulations can allow the designer to predict interactions of molecules not present on the array, such as molecular interactions important in diagnostic and therapeutic applications.

In some embodiments, a structure-based understanding of the binding properties may allow prediction interactions, such as antibody protein interactions, critical for applications such as diagnostics and drug discovery.

However, other arrays may also be utilized according to the methods disclosed herein. For example, algorithms and methods disclosed herein can be applied to nucleic acid arrays, protein arrays, and other organic or inorganic monomer or polymer arrays.

Accordingly, embodiments disclosed herein are directed methods of predicting binding on an array, with certain embodiments including contacting a defined array with a training sample containing one or more molecules of interest, wherein the array comprises a plurality of defined molecules; processing interactions between the plurality of defined molecules and the one or more molecules of interest from the training sample according to a data fitting model; and applying the model to interactions between the plurality of defined molecules and a test sample of molecules of interest to predict binding associated with said one or more molecules of interest in the test sample.

In certain embodiments, the defined molecules are selected from the group consisting of one or more of peptides, proteins, and nucleic acids.

We have developed algorithms for relating functional data from libraries of defined molecules to the structures of those molecules. Using this formalism, it has been demonstrated that one can predict the function of molecular species that are NOT present in the library, if those molecules can be described using the same component structures as the molecules present in the libraries. Applications of the embodiments disclosed herein include but are not limited to: Design of new molecular libraries with specific function; Screening of complex molecular systems of known structure for functional prediction; and Discovery of potential lead compounds with desirable functions.

A specific embodiment relates to an array of peptides (amino acid polymers) and their binding properties relative to both monoclonal antibodies and the total circulating antibody population in blood. The specific applications of this embodiment include but are not limited to: Design of peptide arrays that bind to specific antibodies or to serum with specific properties such as the presence of antibodies expressed during a disease state; The enhancement and amplification of the diagnostic and prognostic signals provided by peptide arrays with regard for use in analysing the profile of antibodies in the blood produced in response to a disease, condition or treatment; Discovery of protein antigens or polypeptide sequences that are responsible for the response to a disease, condition or treatment (e.g., discovery of antigens for a vaccine); Discovery of protein antigens or polypeptide sequences that are responsible for adverse reactions resulting from a disease, condition or treatment (e.g., autoimmune reactions); The discovery of lead compounds to be used in the development of therapeutics; The discovery of potential targets of therapeutic treatment; and The characterization of specific antibodies, such as monoclonal antibodies used as therapeutics, to determine what peptide and protein sequences they are expected to bind.

These and other aspects will be further described in the drawings and disclosure below. However, the scope of the claims is not intended to be limited to the embodiments and examples herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings in the following.

FIG. 5 shows an exemplary array based on four amino acids.

FIG. 7 shows Pearson correlation between the fit and the measured values.

DETAILED DESCRIPTION OF THE INVENTION

Figure 1:
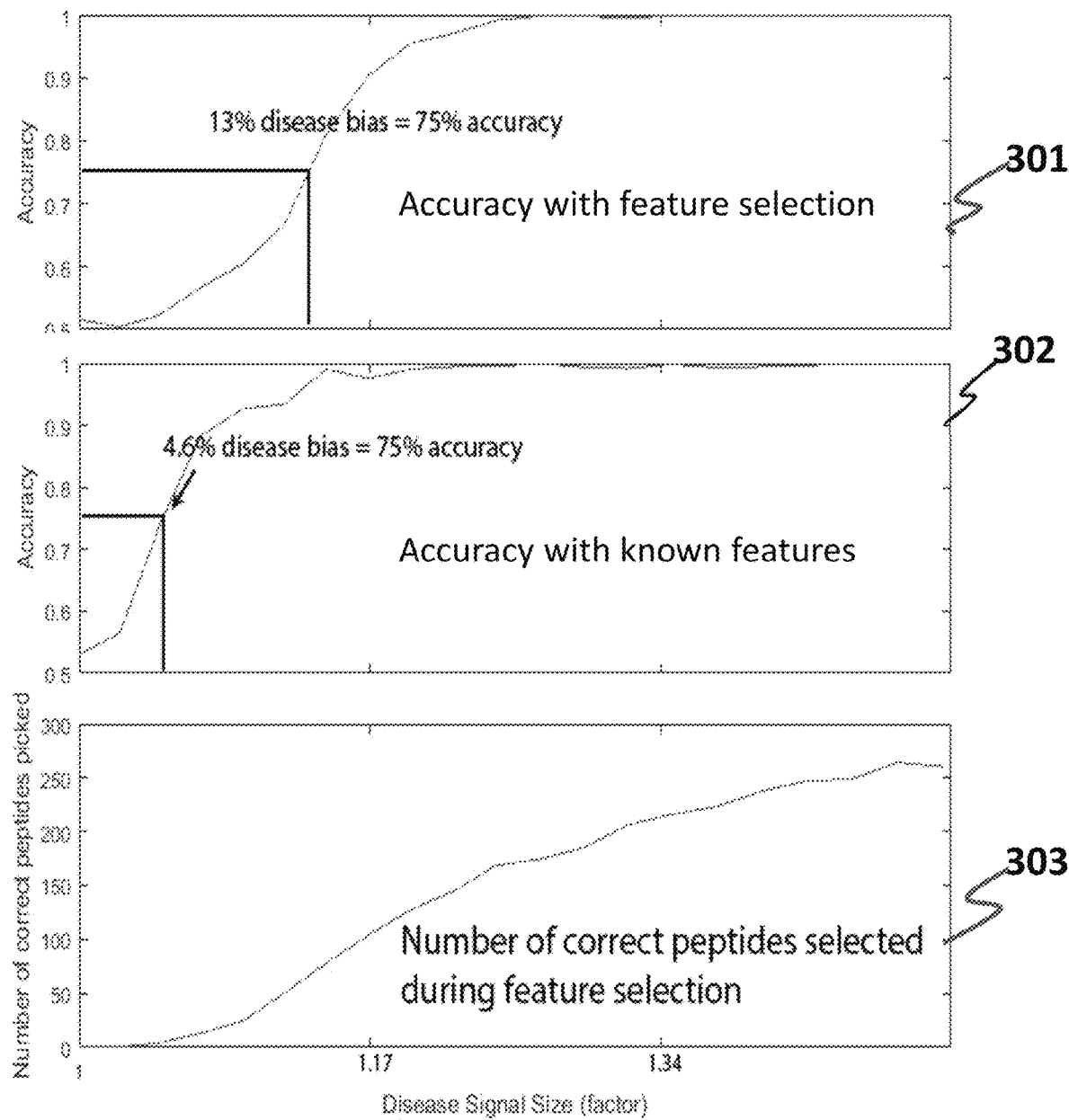
FIG. 1 shows an example of array characteristics based on a simulation as disclosed herein.

Disclosed herein are methods, systems and devices for developing and optimizing array features for detection and analysis of binding molecules in a complex biological sample (for example, antibodies) to targets on an array (for example, peptides).

Immunotherapy and antibody-based treatment of cancer have been two major therapeutic breakthroughs in extending patient survival. Immunotherapy activates and utilizes the patient's immune system to kill cancer cells, whereas antibody-based therapeutics target specific pathways that inhibit or kill cancer cells. Each of these approaches rely heavily or exclusively on the discovery and development of highly target-specific antibodies or biologics and more recently, multi target-specific antibodies or biologics with multivalent binding. Even with the significant advancement in patient survival offered by immunotherapy and antibody-based treatment, specific major challenges remain.

Synthesized peptide libraries are commonly used for antibody binding characterization, but this is expensive and limited to a small sample of sequence space (i.e., epitope mapping/binning). Antibody characterization with synthesized peptide libraries is currently performed with relatively low-throughput methods such as surface plasmon resonance and interferometry. Protein and peptide microarrays can be used to characterize greater than 10,000 antibody-peptide interactions, but protein and robotically printed peptide arrays have been cost-prohibitive and in situ synthesized peptide arrays can suffer from lack of scalability, reproducibility and production quality. However, the ability to both design the composition of the arrays to meet specified applications and the ability to use the information gained from the arrays to make predictions about interactions not directly on the array should help address or overcome past issues with protein and peptide arrays.

Some embodiments disclosed herein are based on computer simulation for selecting chemical structures on peptide array construction. The simulation results enable reliable, high-throughput, low-cost and comprehensive binding characterization of therapeutic antibody and biologic lead candidates. For example, benefits of the technologies include: 1) Designing a better process for array manufacturing; 2) Improving array features for disease binding; 3) Lowering array costs; and predicting new binding interactions.

Peptide Arrays

The technologies disclosed herein are described in terms of the binding of antibodies in blood to peptides on an array. In principle, however, it is equally applicable to other situations in which there are a set of fixed chemical structures interacting with a complex mixture and some measurement is then made from each of the fixed chemical structures or a subset of those structures.

In some embodiments, the complex biological sample may comprise blood, serum, plasma, lymph fluid, interstitial fluid, amniotic fluid, sweat, tears, peritoneal fluid, sebum, cerebral spinal fluid, urine, saliva, feces, synovial fluid, pus, nasal drainage or phlegm, pleural fluid, waste water, effluent or other complex fluidic sample.

In various embodiments, the technologies disclosed herein analyze, include or use circulating antibodies in blood or a bodily fluid, including immunoglobulins such as immunoglobulin G (i.e., IgG class). There are on the order of $10^9$ different IgG molecules in blood, most of which are present at very low concentrations in a blood sample. The total concentration of IgG in blood is on the order of 10 mg/ml or about 70 micromolar. Antibodies are present in a huge diversity of concentrations. For example, a relatively small number of antibodies (10-100) can make up a few percent of the total IgG during an active infection.

In various embodiments, the technologies disclosed herein include a peptide array. In some embodiments, a peptide array comprises a fixed area, for instance 0.2 $cm^2$, 0.3 $cm^2$, 0.4 $cm^2$, 0.5 $cm^2$, 0.6 $cm^2$, 0.7 $cm^2$, 0.8 $cm^2$, 0.9 $cm^2$, 1.0 $cm^2$, preferably 0.5 $cm^2$. In some embodiments, a peptide array comprises molecules arranged as features in a regular array with at least 20%, at least 30%, at least 40%, at least 50%, at least 60%, at least 70%, at least 80% or at least 90% of the area covered by the peptide features and at least 10%, at least 20%, at least 30%, at least 40%, at least 50%, at least 60%, at least 70% or at least 80% by interstitial space.

In some embodiments, a density (e.g., the number of individual peptides per square nanometer) is a variable in the analysis. In some embodiments, the density of the peptides is centered at 0.1, 0.2, 0.3, 0.4, 0.5, 0.6, 0.7, 0.8, 0.9, 1.0, 1.2, 1.5, 1.8, 2, 2.5, 3.0, 3.5, 4.0, 4.5, 5.0, 5.5 or 6.0 nanometers. In yet other embodiments, the distance between peptides is not more than 0.5 nanometers, not more than 1.0 nanometer, not more than 1.5 nanometers, not more than 2 nanometers, not more than 2.5 nanometers, not more than 3 nanometers, not more than 3.5 nanometers, not more than 4 nanometers, not more than 4.5 nanometers, not more than 5 nanometers, not more than 5.5 nanometers, not more than 6 nanometers, preferably not more than 0.5 nanometers, 1.0 nanometer or 1.5 nanometers. In a peptide array, the peptides are assumed to be arranged generally randomly such that the Kd values with respect to particular Abs (see below) have a generally continuous distribution. In other embodiments, the peptide arrays may contain pseudo-random peptides arranged such that the Kd values with respect to particular Abs (see below) have a generally continuous distribution. In yet other embodiments, the peptide sequences in the peptide arrays may be pre-derived.

In some embodiments, it is assumed that all peptide features contain the same number of peptides and thus the same number of Ab binding sites. In some embodiments, the number of moles of each peptide on the surface depends on the size of the features. In some examples, the number of moles of each peptide on the surface may be approximately $5\times10^{-16}$, or a total of $5\times10^{-11}$ moles of total peptide.

Incubation Chamber and Assay Process

In various embodiments, the technologies disclosed herein include an incubation chamber for an array processing. The volume of the chamber over the peptides is considered a variable, but is preferably at 150 microliters. In yet other embodiments, the volume of the chamber is 50 microliters, 60 microliters, 70 microliters, 80 microliters, 90 microliters, 100 microliters, 110 microliters, 120 microliters, 130 microliters, 140 microliters, 150 microliters, 160 microliters, 170 microliters, 180 microliters, 190 microliters, 200 microliters, 210 microliters, 220 microliters, 230 microliters, 240 microliters, 250 microliters, 300 microliters, 325 microliters, 350 microliters, 375 microliters, 400 microliters, 425 microliters, 450 microliters, 475 microliters, 500 microliters, 900 microliters, or more. Alternatively, a flow cell may be used in washing.

In some embodiments, a binding simulation is performed assuming a constant temperature. In other embodiments, the temperature of the assay varies throughout the course of the assay. In yet other embodiments, the temperature of the assay is ambient temperature. In some embodiments, washes are either done in infinite volume or a fixed volume, also centered at 150 microliters, which is described as a variable in a simulation model. In yet other embodiments, wash volumes include 100 microliters, 150 microliters, 200 microliters, 250 microliters, 300 microliters, 350 microliters, 400 microliters, 450 microliters, or 500 microliters.

In some embodiments, the dilution of the blood applied to an array is a variable. In some embodiments, the blood sample is diluted by 1×, by 2×, by 3×, by 4×, by 5×, by 6×, by 7×, by 8×, by 9×, by 10×, by 20×, by 30×, by 40×, by 50×, by 60×, by 70×, by 80×, by 90×, by 100×, by 150×, by 200×, by 300×, by 400×, by 500×, by 600×, by 700×, by 800×, by 900×, by 1000×, by 1100×, by 1200×, by 1300×, by 1400×, by 1500×, by 1600×, by 1700×, by 1800×, by 1900×, by 2000×, by 2500×, by 3000×, by 3500×, by 4000×, by 4500×, by 5000×, by 5500×, by 6000×, by 6500×, by 7000×, by 7500×, by 8000×, by 8500×, by 9000×, by 9500×, by 10,000×, by 20,000×, by 30,000×, by 40,000×, by 50,000×, by 60,000×, by 70,000×, by 80,000×, by 90,000×, by 100,000×, by 200,000×, by 300,000×, by 400,000×, by 500,000×, by 600,000×, by 700,000×, by 800,000×, by 900,000 or by 1,000,000×. Preferably, the blood is diluted by 660×, giving a final IgG concentration of about 70 nM.

In some embodiments, an effective peptide concentration in 150 microliters (total peptide) is about 250 nM. Thus for the studies the peptide is generally in excess. In general, as discussed below, only about 1% of the peptides on average are bound to Ab; of course in various embodiments, some peptides are much more and some much less.

In some embodiments, the binding time of the assay is variable. In some embodiments, the binding time is 10 minutes, 20 minutes, 30 minutes, 40 minutes, 50 minutes, 60 minutes, 1 hour, 2 hours, 3 hours, 4 hours, 5 hours, 6 hours, 7 hours or more. Preferably, binding time of the assay centered at 1 hour and varied. In other embodiments, the wash time of the assay varied from 1 minute, 2 minutes, 5 minutes, 7 minutes, 10 minutes, 15 minutes, 20 minutes, 25 minutes, 30 minutes, 45 minutes, 1 hour or more. Usually the wash was considered to be against an infinite dilution and performed for 15 minutes (also varied) though small volume washes and longer times were also considered.

Array/Library Normalization

In some embodiments, provided herein are methods, systems and devices for array or library normalization strategies with regard to particular molecular structures and specific signals. Consider for example, a series of molecular structures. These structures could be organizing on a surface, such as in an array, or on beads, or could be in another format where each type of structure or groups of related structures can be assayed resulting in a set of values. The molecules could be of any composition, so long as there is a particular structure or somehow related family of structures associated with each measurement. In some embodiments, the assay or measurement involves binding to a chemical or mixture of chemicals or complex fluidic samples. In yet other embodiments, the assay or measurement involves chemical reactivity, for example, chemical reactions that are structurally dependent, such as covalent modification, catalysis or other structural modifications. Fundamentally, any signal that derives specifically from the interaction of a specific molecular structure with the material added will result in a set of values associated with a set of structures.

In some embodiments, the binding reaction to the array structures can be detected in any of a number of ways. In one embodiment, a labeled ligand is used to detect antibodies binding to peptides on an array surface. In other embodiments, a secondary antibody that binds to all of the antibodies (or a specified subset, such as all IgG) present is used to detect antibodies binding peptides on an array surface. In yet other embodiments, the signals can be read from the intensity of the label (e.g., a fluorescence label read by an array reader that is commercially available). In still other embodiments, analysis of the relationship between the properties of the structures and the level of the signal is determined.

In some embodiments disclosed herein are arrays of peptides that bind to antibodies in a sample, for example blood, in a manner that depends on at least some aspect of the peptide array structure or structural characteristics. Linear peptides, for example, consist of a set of amino acids linked together in a particular order.

In this case, one might relate the binding of the antibody in the fluid sample to various aspects of the structure such as $$F_i = S_i * \Sigma_j a_j C_{i,j} \tag{1}$$

Here the signal of the $i^{th}$ peptide is $F_i$, the composition of the $i^{th}$ peptide is given by the j values, and $C_{i,j}$ each of those j composition values is modified by a coefficient $a_j$. The sum shown above represents the part of the signal that can be described by the composition of the peptide without regard to order of the amino acids of the peptide. $S_i$ represents the part of the signal that is due to the sequence (order) of amino acids beyond what is determined simply from the composition of amino acids. In some embodiments, the functional form shown here is only one of a number of possible functional forms.

In other embodiments, another possibility for relating the binding of the antibody in the fluid sample to various aspects of a structure is $$F_i = S_i + \Sigma_j a_j C_{i,j} \quad (2)$$

Either functional form, as well as a number of others, could be used to describe the system equally well, but the nature of the modifier $S_i$ changes depending on the form of the above equation (1) or (2). The log of the fluorescence is used when the relationships considered are likely to be linear functions of the free energies of a set of interactions.

In some embodiments, analysis is narrowed to only that part of the signal that is dependent on the order of amino acids. In these embodiments, specific antibody binding is thought to be highly sequence dependent rather than just composition dependent. In either formulation, this might be done by first fitting the signal to the composition using a linear fit of $F_i$ to the coefficients $a_i$ in the expression $$f_i = \Sigma_j a_j C_{i,j} \quad (3)$$

Where $f_i$ are the calculated values and an expression such as $$\Sigma_i (F_i - f_i)^2 \quad (4)$$

is minimized and then the values of $f_i$ derived are used to modify the measured values $F_i$ in such a way as to remove the influence of composition from the signal.

For example, if equation (1) is used to describe the array, one might normalize the array such that each measurement $F_i$ in the array is replaced by $F_i/f_i$ or if equation (2) is used, $F_i$ could be replaced by $F_i - f_i$. Other formulations of the relationship between the compositionally dependent part of the signal and the remaining part of the signal depending on order would result in different approaches to removing the compositional part by some form of normalization.

In some embodiments, fitting is an approach used for normalization of the analysis. In yet other embodiments, the average or the median of the signal from all peptides that have the same composition is taken and then divided amongst all peptide measurements by that average or median. This would not involve fitting, but would be another form of normalizing the values to remove the part of the signal due to composition alone and leave signal that was due to the order of the amino acid. In still other embodiments, the opposite could be done by the approaches above; one could remove the part of the signal due to order and only consider that part that is describable based on composition.

Those skilled in the art will realize that there are many different ways to characterize a chemical structure. For example, instead of considering the measurement as a function of the order and the composition, one might consider the measurement in terms of the part of the value that depends on the charge and the part that does not. Alternatively, hydrophobicity, length (number of amino acids in the case of a peptide), molecular weight, solubility, or calculated properties of the structure such as volume, flexibility, and many other chemical and structural properties of the molecules in the array or library could be used in a similar fashion. There is a substantial literature on the subject of chemical descriptors used for different kinds of molecular structures. For example, one list of descriptors used to describe peptides is given by Sanberg et al., 1998, J. Med. Chem. 41, 2481-2491. Some descriptors used in other small molecule libraries are discussed and reviewed by Gozalbes and Pineda-Lucena, Comb. Chem. High Throughput Screen., 2011, 14, 548-458. One descriptor could be used or combinations of descriptors could be used by, e.g., adding additional sum terms over various descriptors to equations (1) or (2). As noted above, one could selectively remove one part or another of the signal, as appropriate for the application.

Composition as a Function of Position

In some embodiments, provided herein are methods, systems and devices including composition as a function of position. Referring to FIG. 5, consider peptides that are 4 amino acids long made of only 4 amino acids: "N," "E," "A," and "L." Given a set of peptides in configurations 701, 702 and 703, and fitting a matrix of coefficients 704, binding values can derived by the sum of each term in a particular peptide matrix times each term in the coefficient matrix. The biding values are: AEEL 1.17, LNEA 0.44, and ENNA 0.24.

In some embodiments, for an array that uses 16 amino acids and a model that considers compositions in 7 positions, the number of coefficients per position and the total number of coefficients are summarized in Table 1. The number of coefficients increases exponentially with the number of monomers involved.

TABLE 1

|  | # of coefs. per position | Total # coefs. |
| --- | --- | --- |
| 1-mers | 16 | 112 |
| 2-mers | 256 | 1792 |
| 3-mers | 4096 | 28672 |

The evaluation in Table 1 is based on simple, linear models fitting to the log of the fluorescence (free energies add and are like logs of concentrations), provides a useful starting point for the algorithm described herein.

In some embodiments, the technologies involve the following process: (a) A study randomly splits peptides of an array in half (e.g., 50% training peptides and 50% testing peptides), and (b) randomly splits the samples into two parts (e.g., 75% training samples and 25% testing samples, where the percentages are adjusted based on studies). Then, the process (c) fits all samples on the training peptides (this becomes the reduced training set), and (d) fits all samples on the test peptides (this becomes the reduced test set). The process then (e) selects the best coefficients to use in classification from the training samples run on the training peptides, and (f) generates a classifier using the best coefficients from the training samples on the training peptides. Finally, the process (g) applies the classifier to the coefficients from the test samples on the training peptides, and (h) applies the classifier to the coefficients from the test samples on the test peptides. The steps (b) to (h) are repeated the four-fold cross validation 10,000 times.

One benefit of the methods and technologies disclosed herein is to define array sequences. For instance, an array can be redesigned by the following process. The first step starts with a random array of hundreds of thousands to millions of features and a large sample set of a group of diseases that a user wishes to separate with the designed array. The second step is to fit samples to the predictive models. The third step uses the model to design a set of peptides that more easily distinguishes the diseases in question and evaluates the following: (a) design of a peptide set per array of about ~20,000 in number (such that many more arrays can be manufactured per wafer, lowering production costs) (b) Use of about 10 of the amino acids and excluding the synthetically challenging ones. (c) Evaluation of the array for low and even background binding (d) Evaluation of whether all peptides sit comfortably in the dynamic range of binding (e) Evaluation of a set of samples that can be used to normalize the whole distribution.

Another benefit of the technologies is to search for antigens. For example, a user can tile the proteome of HBV and HCV into overlapping 9-mers. A user can use the algorithm from the array fit to predict binding to each 9-mer for each of the 44 samples. In some embodiments, a user performs t-tests to pick those 9-mers that most distinguish people infected with HBV from those infected with HCV.

A specific embodiment of studying the hepatitis B (HBV) vs. hepatitis C (HCV) panel is described as follows. The study includes samples comprising 44 HBV and 44 HCV seropositive donors. Samples were obtained from a commercial blood bank along with the signal over cutoff (SC/O) values for HBV and HCV immunoassays. An array comprised about 130,000 peptides on the array surface. Individual samples were diluted 1:1 with ethylene glycol as a cryo-protectant and aliquoted upon receipt and stored at −20° C. until needed. Selected samples were diluted in assay incubation buffer to 1:100 and aliquoted as single use volumes in a 96 well plate. Samples were arrayed such that each of the four slides assayed would have 11 HBV and 11 HCV donors. Plates were stored at −80° C. until needed. On the day of assay the single use plates are thawed on ice and samples further diluted 1:625 in assay buffer and applied to the array. Bound serum IgG is detected using an IgG specific secondary antibody that is labeled with a fluorophore. Automatic liquid handling systems are used for all sample dilution, reagent application and slide washing steps. Following the final wash and drying of the slides, slide images are obtained using a microarray scanner. Images are gridded using a gene array list file and tabulated data stored as a tab delimited text file. Table 2 shows the results of this study. The classification accuracy is based on area under ROC curve. When using more monomers, the accuracy increases.

TABLE 2

| Dataset | AUC Data from fit | AUC Original minus fit |
|---|---|---|
| Full med norm dataset | 0.78 | |
| Recalculated data from 1-mer fit | 0.63 | 0.73 |
| Recalculated data from 2-mer fit | 0.73 | 0.74 |
| Recalculated data from 3-mer fit | 0.75 | 0.75 |

Digital Processing Device

In some embodiments, the systems, platforms, software, networks, and methods described herein include a digital processing device, or use of the same. In further embodiments, the digital processing device includes one or more hardware central processing units (CPUs), i.e., processors that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In some embodiments, the systems, platforms, software, networks, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLES

Example 1: Modeling of Chemical Structure Selection

Experiments were performed to demonstrate that selecting the correct features to analyze is essential to the success of the assay. This example used data from 156 human blood samples that were applied to an array of approximately 130,000 peptides. For this example, half of the features had a theoretical "disease" signal added to 300 randomly selected peptides. The disease signal was random in size over a Gaussian distribution, i.e., some peptides having an increasing and some peptides having a decreasing signal. The size of the signal was also randomly distributed among the samples that received it, meaning that some human blood samples received much stronger signals in certain features than others. This data set was then treated like a real data set and analyzed first by selecting a subset of statistically promising features using a T-test and then using support vector machine classification to train on those features.

75% of the samples are used for feature selection and training. The other 25% was a test set. The features used for training and testing were randomly selected 100 times and the results averaged to give the final accuracy.

The results are shown in FIG. 1. The panel 301 shows what happens if the above process is carried out and the relative size of the disease signal is increased (shown relative to the background signal). A disease signal 13% of the background in this case is detectable with 75% accuracy (50% accuracy would be random). However, referring to panel 302, if one instead knew exactly which features to pick ahead of time (since in this dataset the disease signal is fabricated, we can know this), instead of relying on statistical tests to find the features, one is able to achieve 75% accuracy using a disease signal that is only 4.6% as large as the background signal, a considerable improvement. The bottom graph 303 shows how many of the 300 "true" disease signals were found by the statistical test as a function of the size of the theoretical disease signal. One can see that even at the largest signal levels used, not all 300 features were correctly identified.

Example 2: Normalization of Array Feature Characteristics

A dataset involving Ovarian Cancer blood samples, 62 case and 94 control, was used in which each sample was exposed to an array of ~130,000 peptides on a surface. The peptides were synthesized with 16 of the 20 natural amino acids (A, D, E, F, G, H, K, L, N, P, Q, R, S, V, W, and Y) and the sequences were chosen to cover combinatorial sequence space as evenly as possible. The IgG antibodies were detected by a specific secondary antibody labeled with a fluorophore and the fluorescence due to that fluorophore was measured with a commercial array reader.

The case and control sample sets were separately fit to a composition model. The model had the form:

$$F_i = \sum_j a_j C_{i,j}$$

Here $F_i$ are the fluorescence values for each of the peptides in the array, $C_{i,j}$ is the composition matrix. The value of $C_{i,j}$ is an integer representing the number of amino acid j present in peptide i.

Different numbers of amino acids, starting at the N-terminus, were used in the determination of the composition of each peptide. If you use just one residue (the N-terminus) and model the binding with 16 coefficients (one for each aa) and then compare the model to the original data using a Pearson correlation, the correlation you get is 0.31. Thus, a small, but significant amount of the binding can be described by just knowing the N-terminal amino acid. Looking at the $2^{nd}$, $3^{rd}$, $4^{th}$ and $5^{th}$ amino acid, the models each one alone generates give a correlation coefficient of ~0.2. In this dataset, the identity of the N-terminus is most important, but individual amino acids at multiple positions are involved in determining the overall binding as well.

Figure 2:
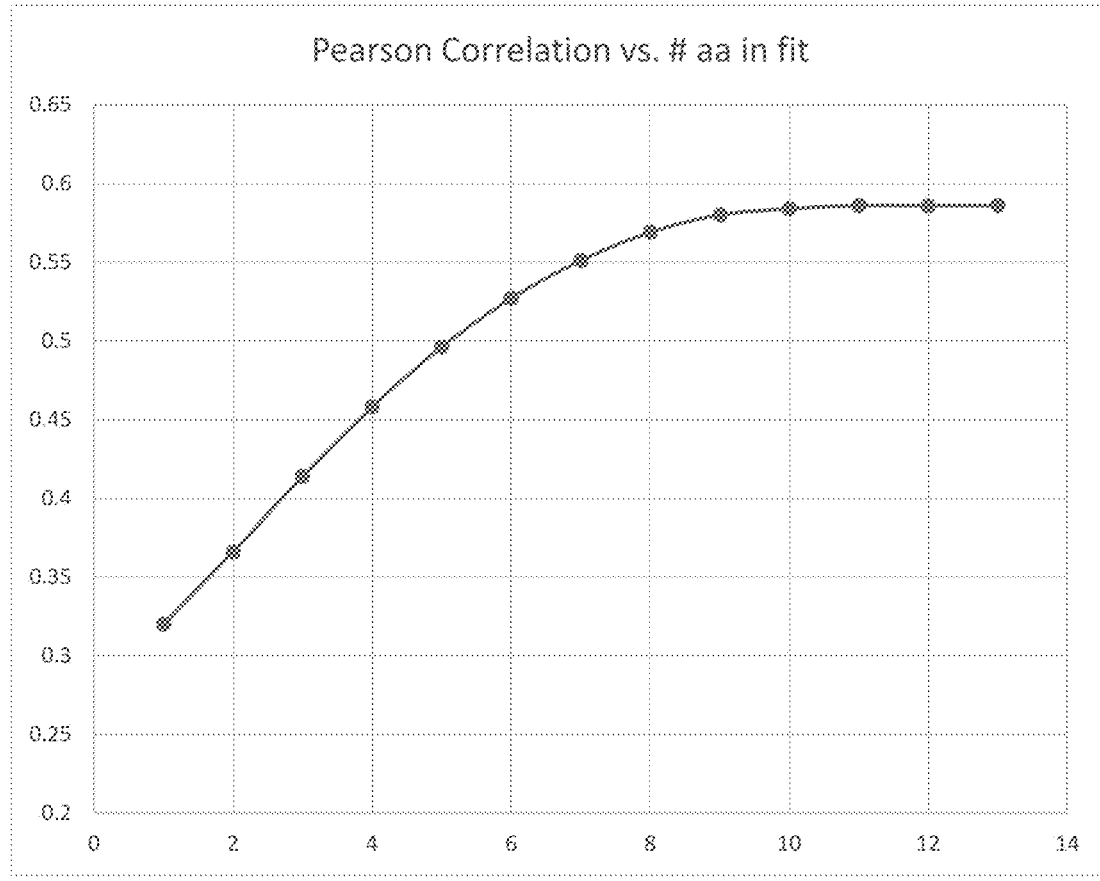
FIG. 2 shows an example of the relationship between amino acid length (x-axis) and accuracy of the model using Pearson Correlation Coefficient analysis.

FIG. 2 shows what happens if you start at the N-terminal amino acid and then use 1, 2, 3, 4, ... 13 amino acids in your compositional modeling (here all amino acids up that that number starting at the N-terminus were used). As you increase the number of amino acids, the model becomes more accurate. Note that there are always just 16 free parameters in the fit (one for each type of amino acid), so the number of fitting parameters may be constant. This fit is length by length: each length of peptide in the array (not all peptides in the array have the same length) is fit separately. By the time you have included the first 10 amino acids, the correlation has maxed at about 0.59.

Figure 3:
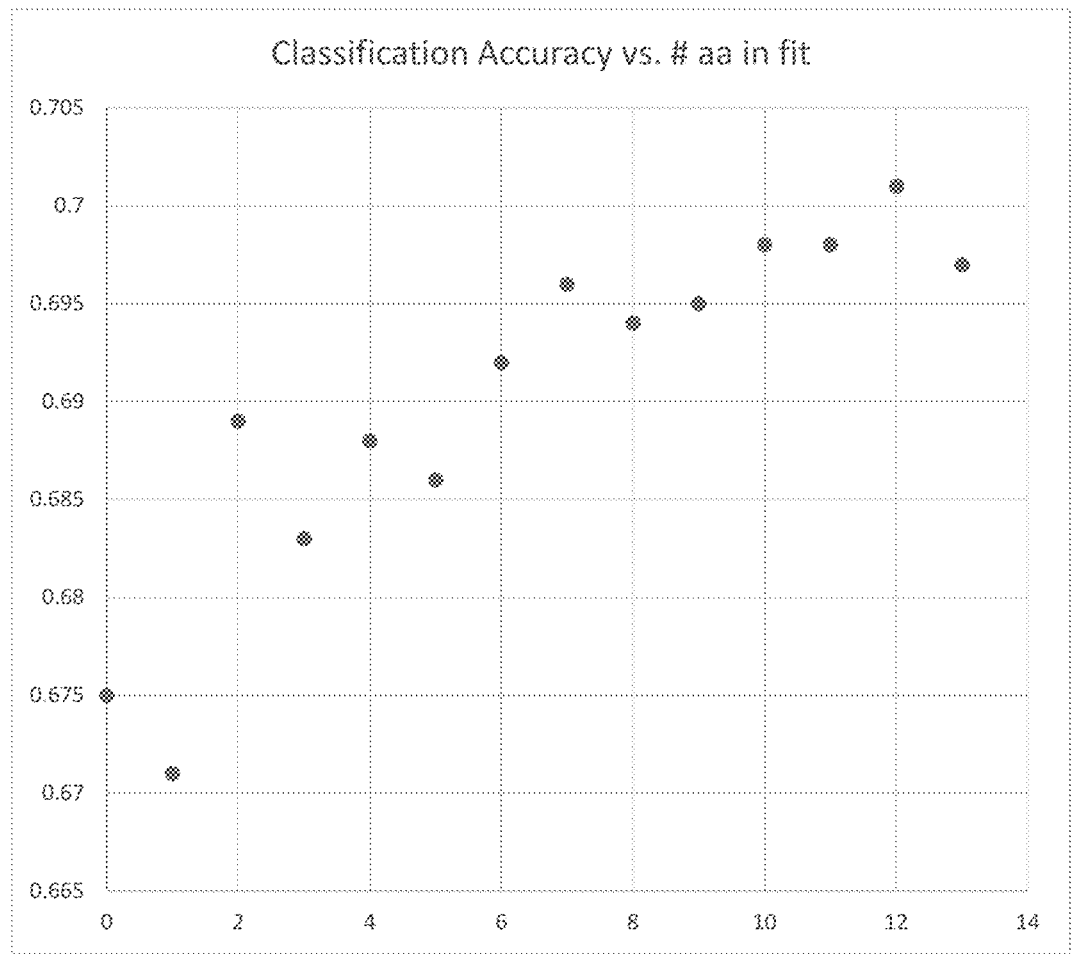
FIG. 3 shows an example of the relationship between amino acid length and accuracy when performing a classification analysis on test peptides.

FIG. 3 shows what happens if you take the original data and divide the actual value for binding to each peptide by the value resulting from the compositional fit and then perform a classification with the data to distinguish case (cancer) from control samples. This classification was done by first selecting those features that gave the greatest difference between case and control via a t-test and then using those features, training a support vector machine classifier. 25% of the samples are left out of the training and used as the test case. This was done repetitively to obtain an average classification accuracy (4-fold cross validation). For the original unmodified data, the accuracy is about 0.68. A substantial amount of the binding variation in the data is removed by taking the ratio, and the classification improves as you perform the normalization. This suggests that removing the compositional part of the data improves performance. Note that the increase in accuracy more or less follows the Pearson correlation of the fit and the original data. The more of the compositional binding removed, the better it gets.

Figure 4:
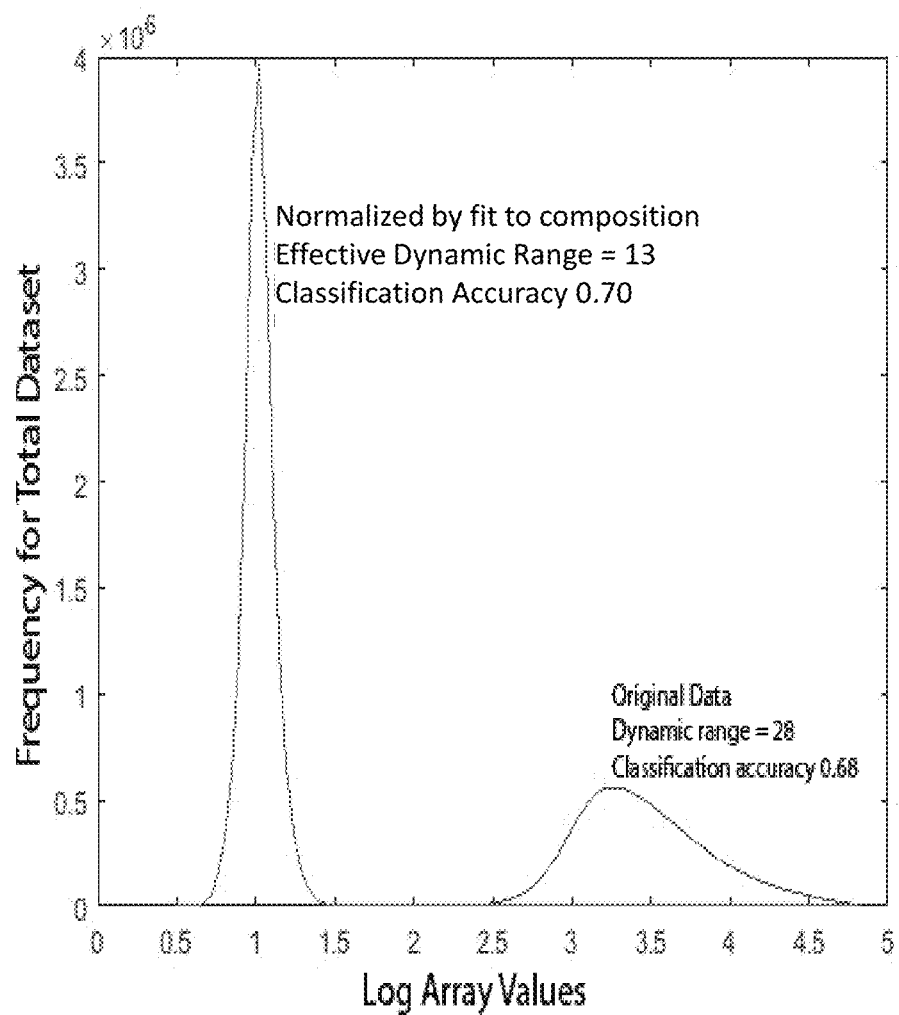
FIG. 4 shows a graphical representation of data prior to analysis ("Original Data") and after normalization for compositional fit of the peptides.

FIG. 4 shows the distribution (log intensity on the x-axis) of the data for the original dataset and the normalized set. The dynamic range of the normalized data decreases by a factor of –2, yet it classifies slightly better. Again, it appears that much of the binding (particularly strong binding) that is seen is compositional and not important in array performance.

Example 3: Fraction of the Molecular Recognition Information Involved in mAb Binding The ability to use data from one set of peptides to predict the binding to a different set of peptide sequences is a measure of how much of the total information content relative to mAb binding is represented by the array as extracted by a particular model.

This example fits the data to a composition model to separate binding from other effects. Data is then averaged for like peptides and like samples. The process further fits each peptide to F=ax+by +cz where a, b, c are parameters and x, y, c are concentrations of the three mAbs (4C1, p53Ab1, DM1A). This model is a simple proportionality model; however, the model may include a constant background term, although the reality is the zero concentration background is small.

Figure 6:
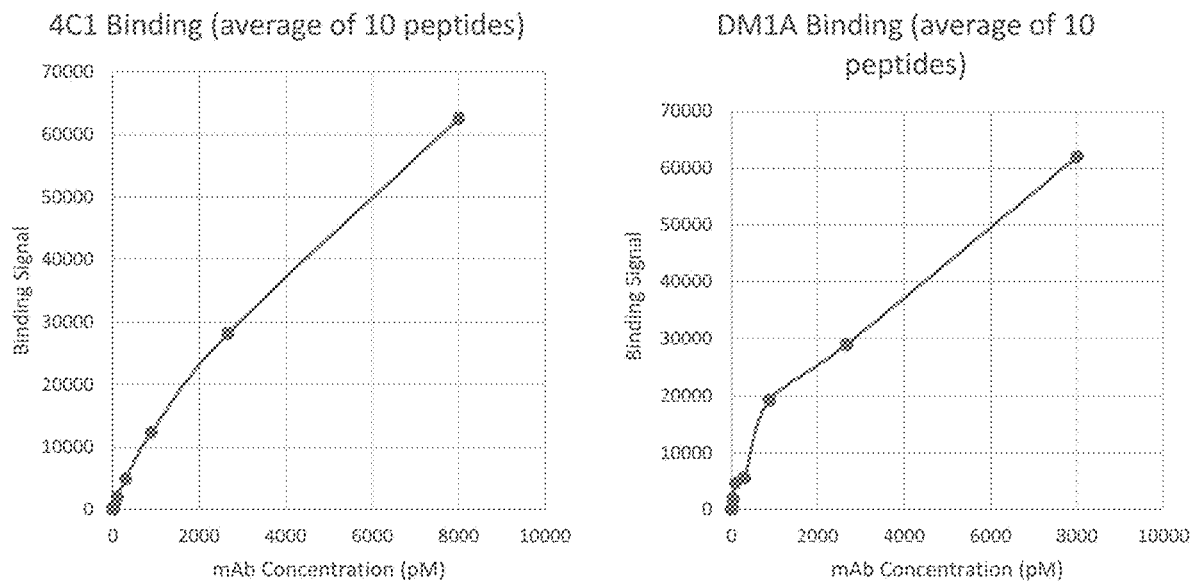
FIG. 6, this example shows concentration dependence with 10 strong binding peptides averaged.

Referring FIG. 6, this example shows concentration dependence with 10 strong binding peptides averaged. The plot 801 shows antibody 4C1, and the plot 802 shows antibody DM1A. While binding is roughly linear at the higher concentrations, it is not proportional to concentration—it increases about 2 times for a 3× concentration change. Thus simple proportionality models are rough measures.

In predicting mAb binding, this example uses the parameters from the fits to represent pure signals from 4C1, p53Ab1 and DM1A. The array comprises about 130,000 peptides. This example randomly splits the array (e.g., 75% training peptides and 25% testing peptides), and then fit the data on the training peptides and predict the binding to the test peptides. Finally, Pearson correlation is used to measure the level of fit.

FIG. 7 shows Pearson correlation between the fit and the measured values. The results show that the fit to concentrations can accurately describe the three highest concentrations fairly well. However, the binding is not strictly proportional to concentration. The slope parameter from the fit is probably a reasonable representation of the sequence dependent binding. There are a small number of peptides that bind specifically; e.g., >10% of the maximum fitting coefficient value. In this example, 4C1 binds 1915 peptides, p53Ab1 binds 39 peptides, and DM1A binds 4104 peptides.

In this example, the model fits to the log of the fluorescence, in analogy to that free energies add and are like logs of concentrations.

Figure 8:
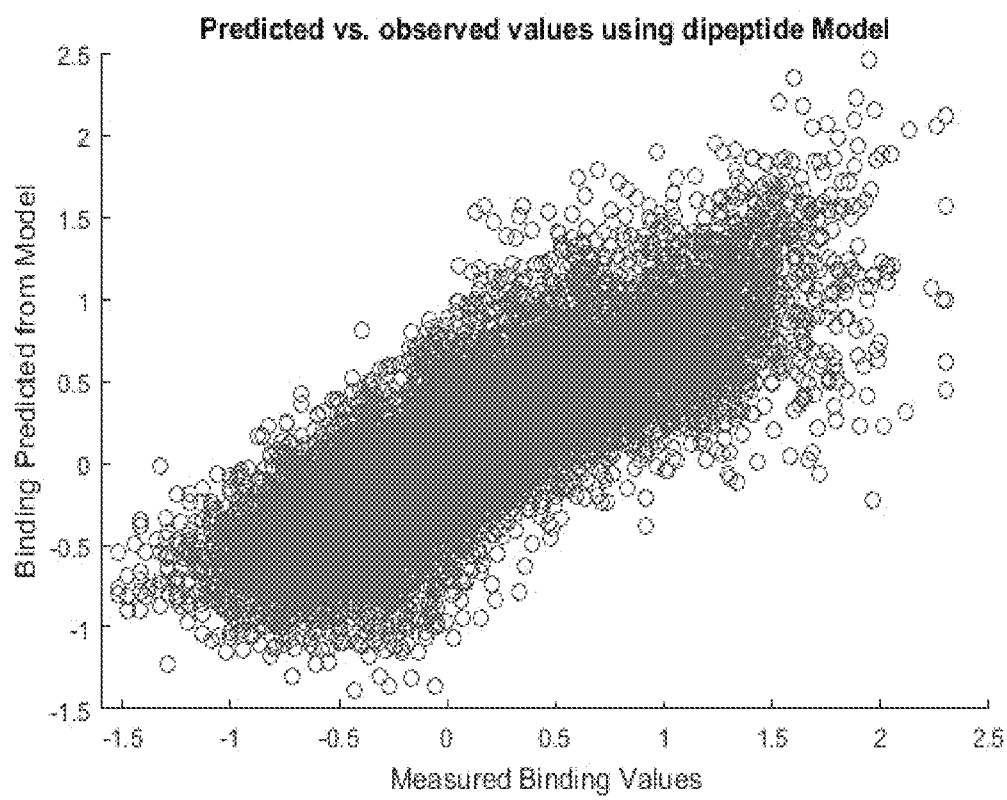
FIG. 8 visualizes the predicted and observed values using dipeptide model.

This example can predict DM1A binding from fits. The Pearson correlations based on monopeptide, dipeptide and tripeptide are shown in Table 3. Overall, the prediction can capture about 70% of the information (using $R^2$ as a measure of information capture). Using one amino acid at all positions or di-peptides predicts without much overfitting using 115,000 peptides to fit and the remainder to test. FIG. 8 visualizes the predicted and observed values using dipeptide model, which shows a nice fit. However, referring Table 3, tri-peptides have strong correlation and start to overfit.

TABLE 3

| | Pearson Correlation | |
|---|---|---|
| Model | Model applied to the peptides fit | Model applied to new peptides |
| monopeptide | 0.78 | 0.79 |
| dipeptide | 0.84 | 0.83 |
| tripeptide | 0.91 | 0.83 |

This example further can predict mAb binding dependent on specificity. Table 4 shows results of different antibodies. The model used herein works best for mAbs that have less sequence specificity. However, for Ab1 that requires an almost exact pentapeptide match, the description is weak. Note that for Ab1, a dipeptide model can actually do better, with correlation using test peptides of 0.64, because there is virtually no overfitting.

TABLE 4

| | | Pearson Correlation, tri-peptide | |
|---|---|---|---|
| mAb | Number of Specific Peptides | Model applied to the peptides fit | Model applied to new peptides |
| p53Ab1 | 39 | 0.78 | 0.56 |
| 4C1 | 1914 | 0.88 | 0.75 |
| DM1A | 4104 | 0.91 | 0.83 |

The best models described above have a Pearson Correlation of 0.83 for the least specific mAB. Specific ones are significantly lower (on the order of 0.64 for the best model). Thus, the range using $R^2$ as a measure of information content is 40-70% depending on the mAb (using the best model in each case). It is pretty clear, however, that prediction can perform better by using more peptides in the array for the tripeptide model. In principle, one can even better for tetrapeptide or pentapeptide models, but the number of coefficients becomes extremely large so one would need to deal with over fitting.

Figure 9:
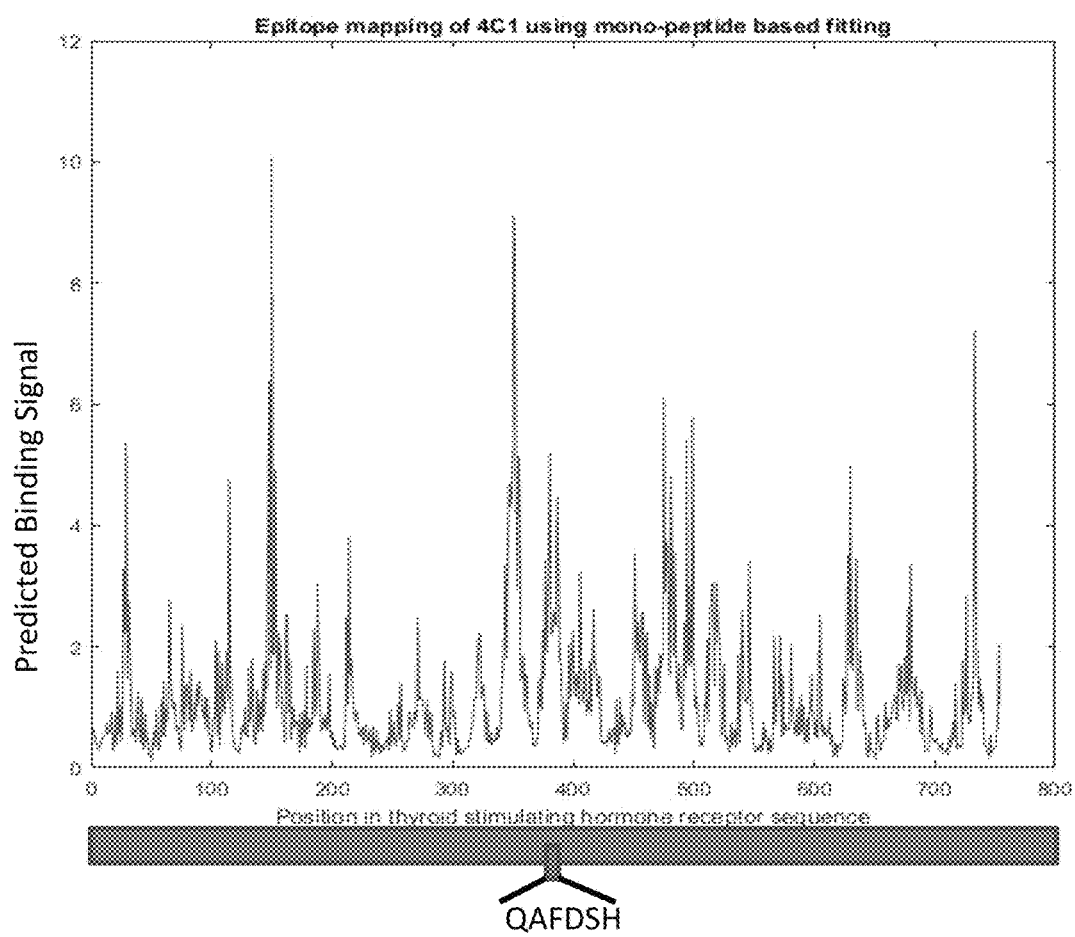
FIG. 9 shows mAb 4C1 epitope prediction using monopeptide fit.
Figure 10:
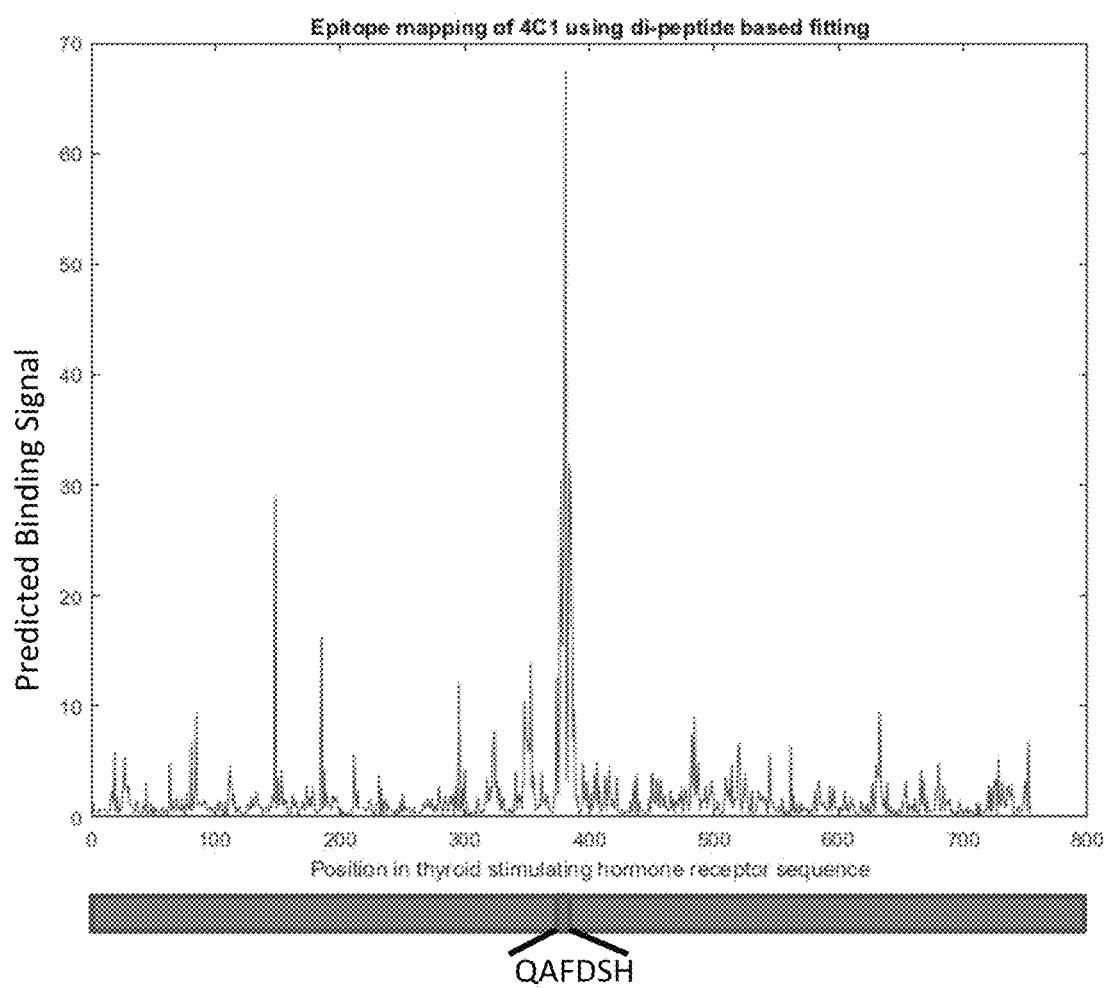
FIG. 10 shows mAb 4C1 epitope prediction using dipeptide fit.
Figure 11:
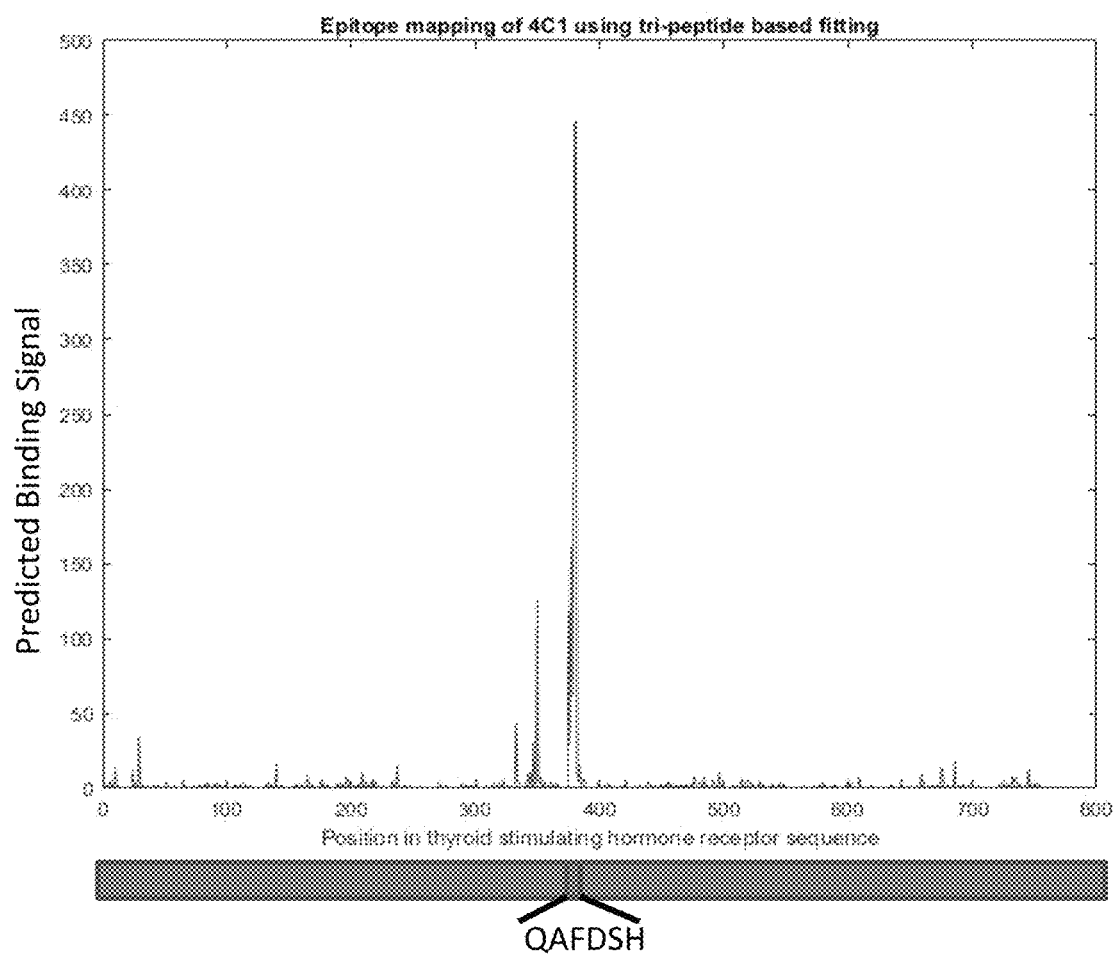
FIG. 11 shows mAb 4C1 epitope prediction using tripeptide fit.
Figure 12:
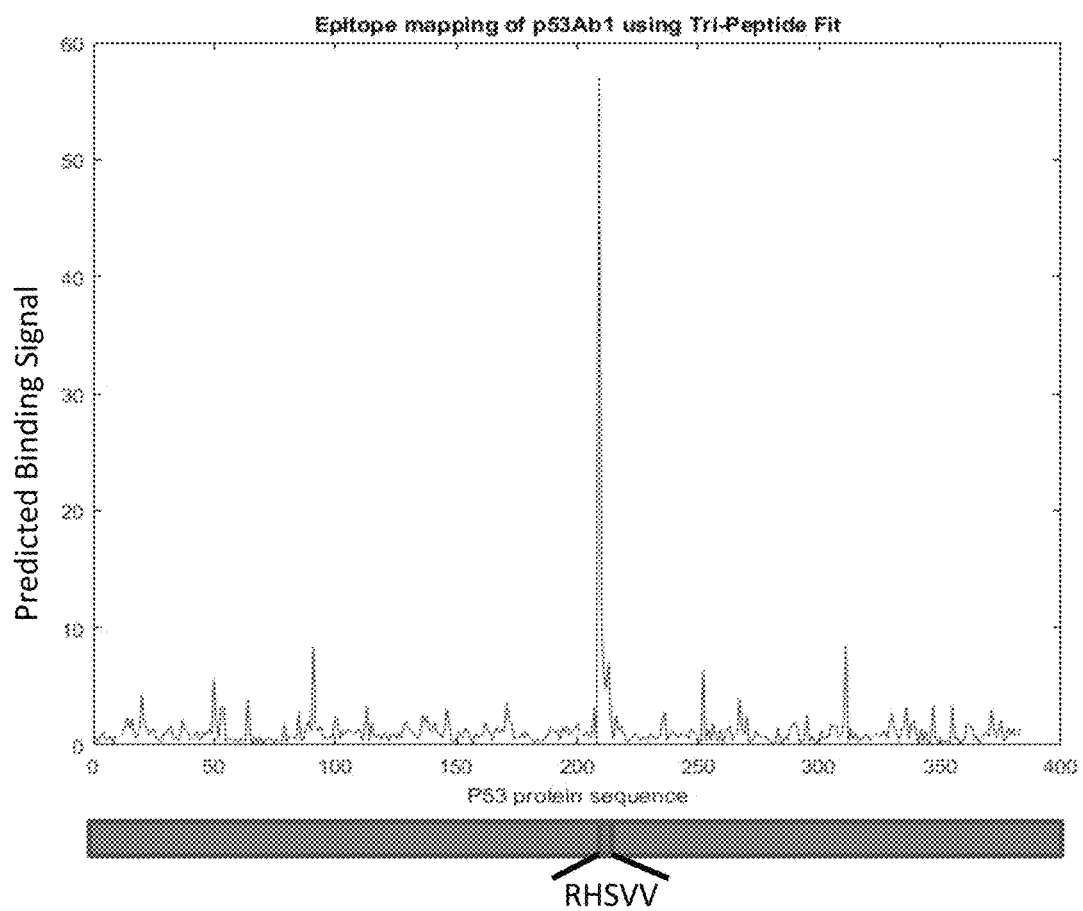
FIG. 12 shows mAb p53Ab1 epitope prediction using tripeptide fit.
Figure 13:
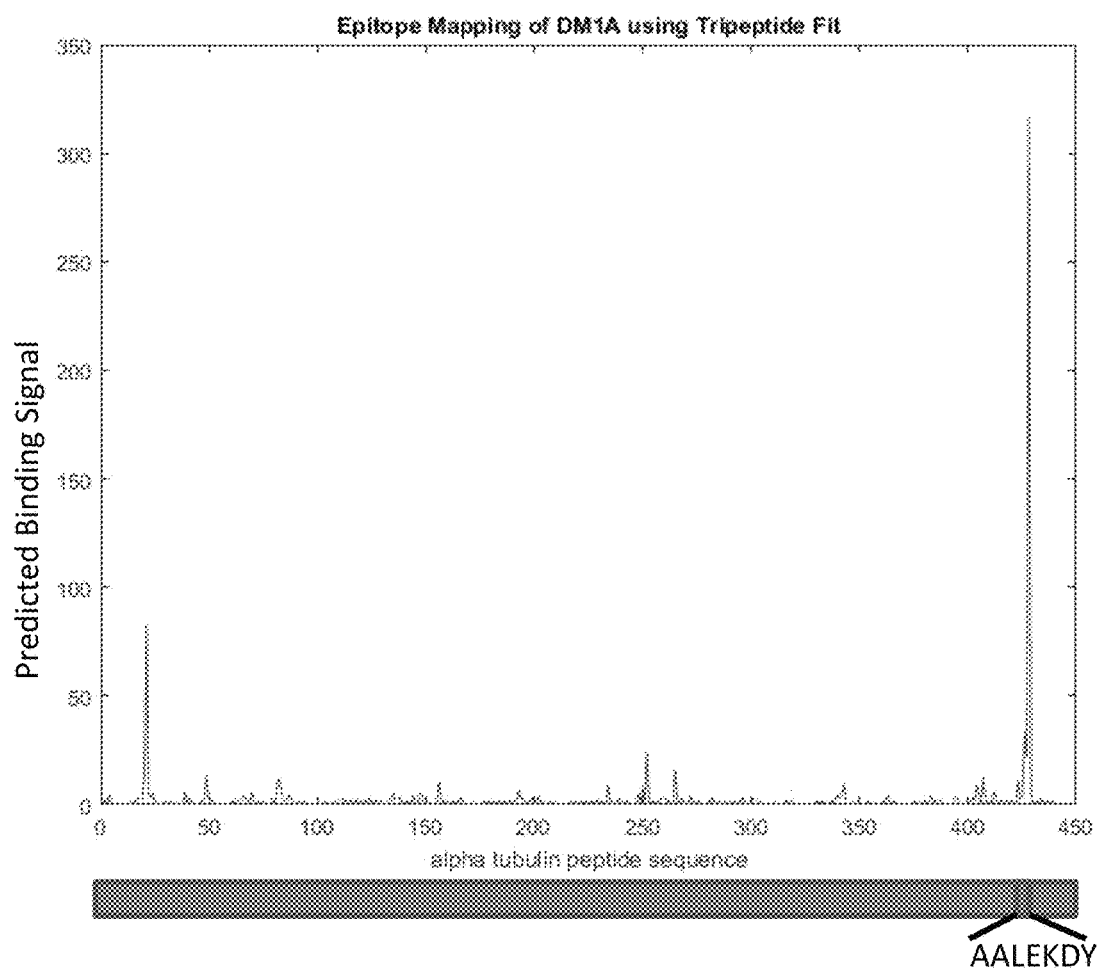
FIG. 13 shows mAb DM1A epitope prediction using tripeptide fit.

The example also shows how algorithms can predict epitopes for monoclonal antibodies. FIG. 9 shows mAb 4C1 epitope prediction using a monopeptide fit (considering the effect of each amino acid at each position in the peptide individually). FIG. 10 shows mAb 4C1 epitope prediction using dipeptide fit (considering the effect of each possible pair of amino acids at each position in the peptide). FIG. 11 shows mAb 4C1 epitope prediction using tripeptide fit (considering the effect of each possible set of three amino acids at each position in the peptide). FIG. 12 shows mAb p53Ab1 epitope prediction using a tripeptide fit. FIG. 13 shows mAb DM1A epitope prediction using a tripeptide fit. Epitope prediction using the tripeptide fit works well, at least for relatively small proteins or proteomes (e.g., it works for individual antigens and for small-sized virus proteome). When using a tri-peptide basis set in the fit, the model works much better than a di-peptide basis set in this regard, and a mono-peptide (individual amino acid) basis set is not useful at all. Going to a tetra-peptide or penta-peptide basis set would likely be even better, but clearly dimensional reduction or much larger peptide arrays would be required (~1-1.5 million peptides for the tetramer fit and about 15-25 million peptides for the pentamer fit).

Figure 14:
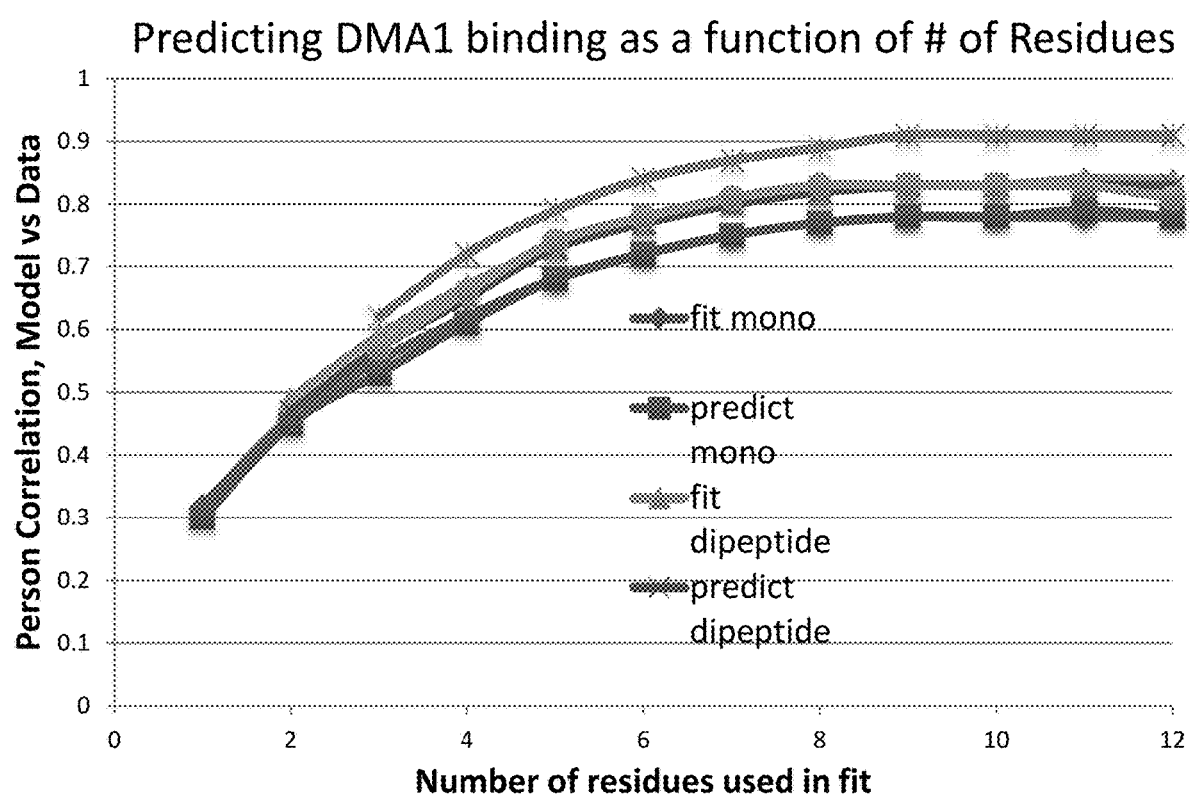
FIG. 14 shows that all models saturate after about the first 9 amino acids.

This example also shows how much of the peptide is involved in defining the predictive power. FIG. 14 shows that all models saturate after about the first 9 amino acids (from the N-terminus). The N-terminal sequence appears to be much more important than sequence near the C-terminus, which is not surprising as 9 is the average peptide length. Each amino acid considered separately is least effective, but has no overfitting. The dipeptide and tripeptide are equally effective at prediction, but the tripeptide is substantially overfit.

Figure 15:
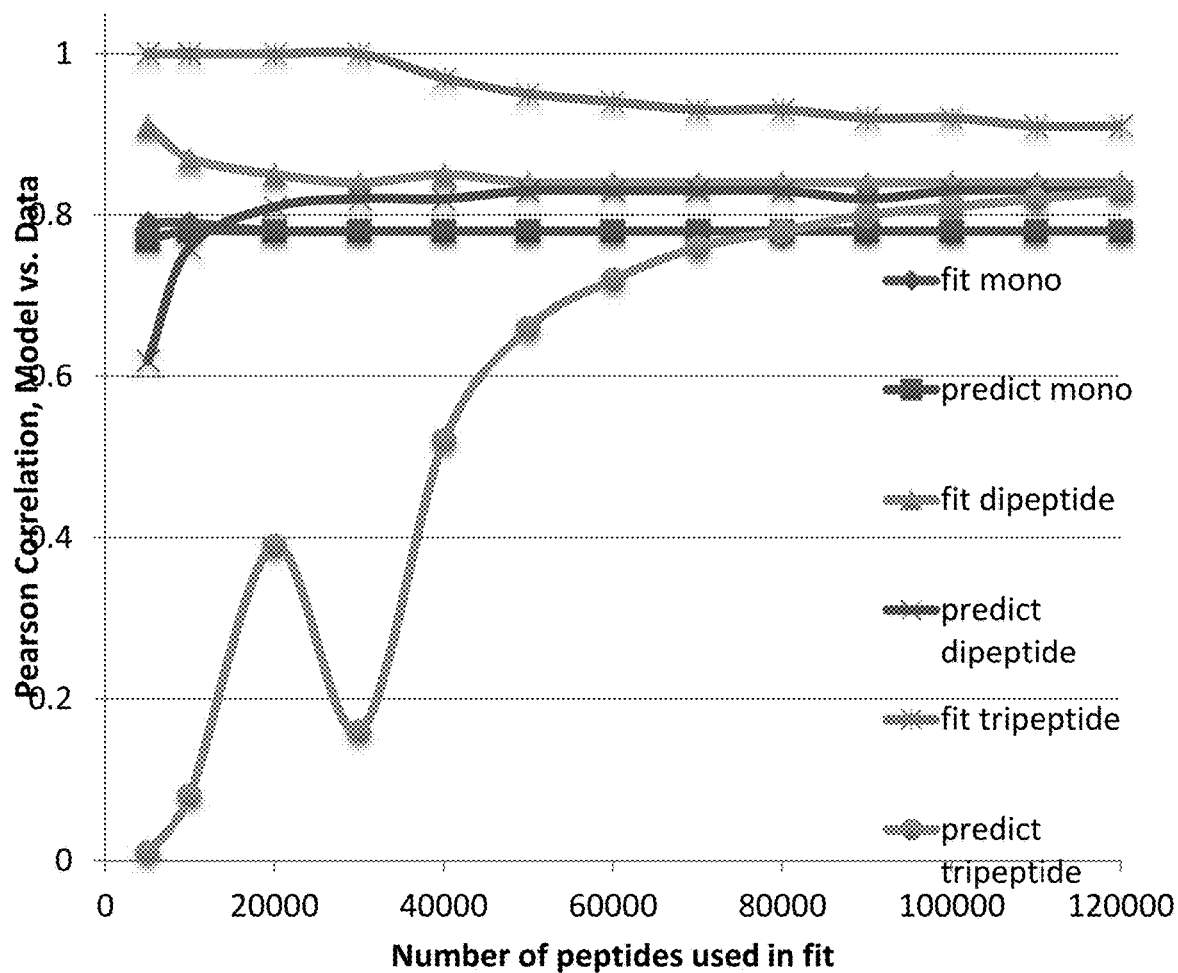
FIG. 15 shows predicting DMA1 binding as a function of number of peptides.

This example also shows how the predictive power depends on the number of peptides used in the fit. FIG. 15 shows predicting DMA1 binding as a function of number of peptides. The monopeptide model fits to <5000 peptides without overfitting. The dipeptide model requires at least 20,000 peptides. The tripeptide model is still overfit at 120,000 peptides and probably would be improved with 3 times more peptides, perhaps getting to about 0.87 for a correlation. Thus, predictive power depends on the model used (mono, di, tripeptide), and depends on a user's choice. In some cases, 5,000 is enough for models based on single amino acids. In some cases, 20,000 is probably enough for models based on di-peptides. In some cases, tri-peptides are overfit even at 120,000 peptides and the convergence suggests one would need 300,000-400,000 peptides Example 4: Fraction of the Molecular Recognition Information Involved in Sera IgG Binding This example considers 44 Hepatitis B virus samples and 44 Hepatitis C virus samples. This test just deals with a mean of all samples. The array used herein comprises ~130,000 peptides. The study randomly splits the array: 90% training peptides and 10% testing peptides. Then this example uses a linear fit in which every mono-, di-, tri-peptide at every position is a basis element in the model. Finally, the model fit all samples on the training peptides, predicts the binding to the test peptides, and measures the Pearson correlation between the actual binding and predicted binding to the test peptides.

Figure 16:
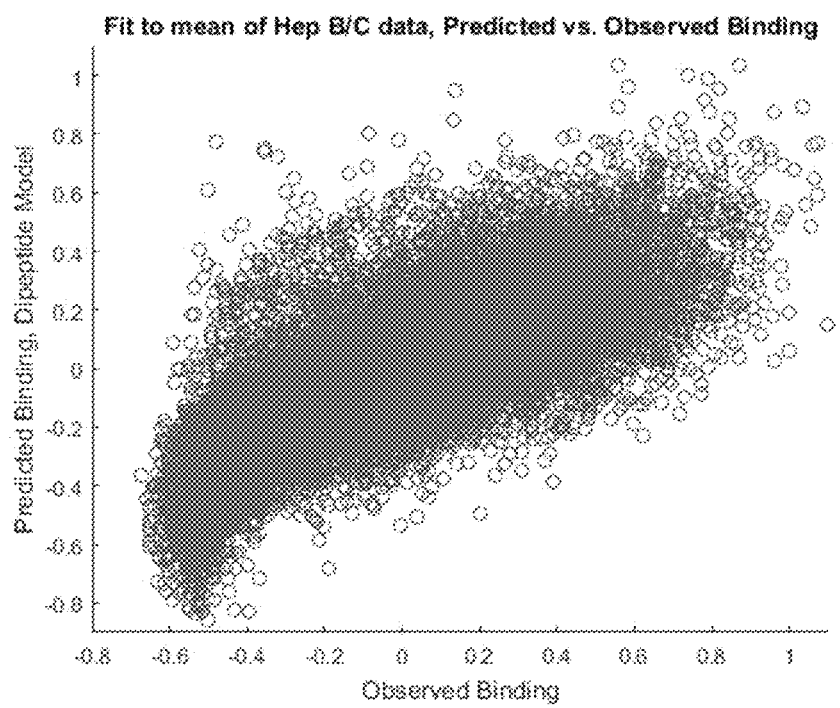
FIG. 16 shows scatter plot of predicted data versus observed using test peptides.

Table 5 shows correlation between model predictions and data. This is for the fit that simultaneously fits all positions using 12 residues and 115,000 peptides as the training set, remainder as the test set. Very similar results (slightly lower) result when fitting positions separately. FIG. 16 shows scatter plot of predicted data versus observed using test peptides.

TABLE 5

| | Pearson Correlation | |
|---|---|---|
| Model | Train | Test |
| mono | 0.72 | 0.71 |
| di-peptide | 0.78 | 0.77 |
| tripeptide | 0.88 | 0.75 |

Figure 17:
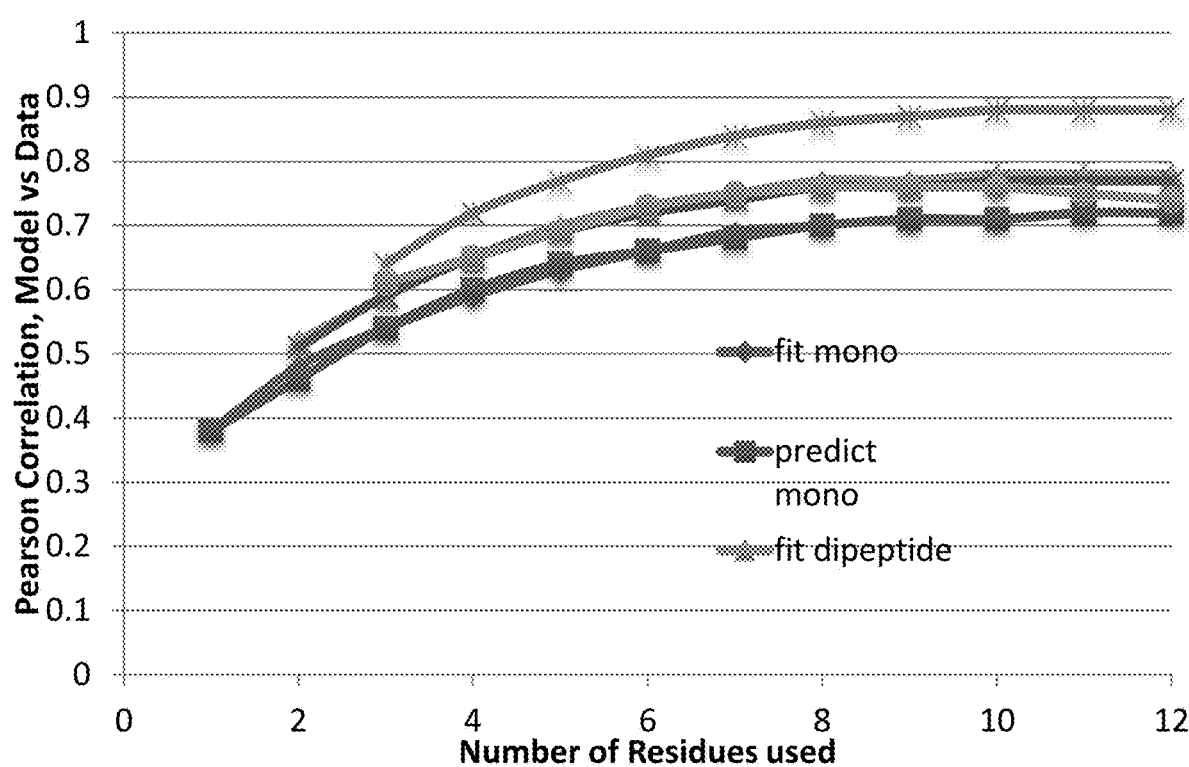
FIG. 17 shows correlation (model vs. data) with increasing number of residues fitting all positions simultaneously.

FIG. 17 shows correlation (model vs. data) with increasing number of residues fitting all positions simultaneously. Similar to the aforementioned DM1A, the di-peptides and tri-peptides give the best results, though by 12 residues, and the tripeptide prediction is worse than at ~9, presumable because of noise. Again, the tri-peptide consistently overfits.

Figure 18:
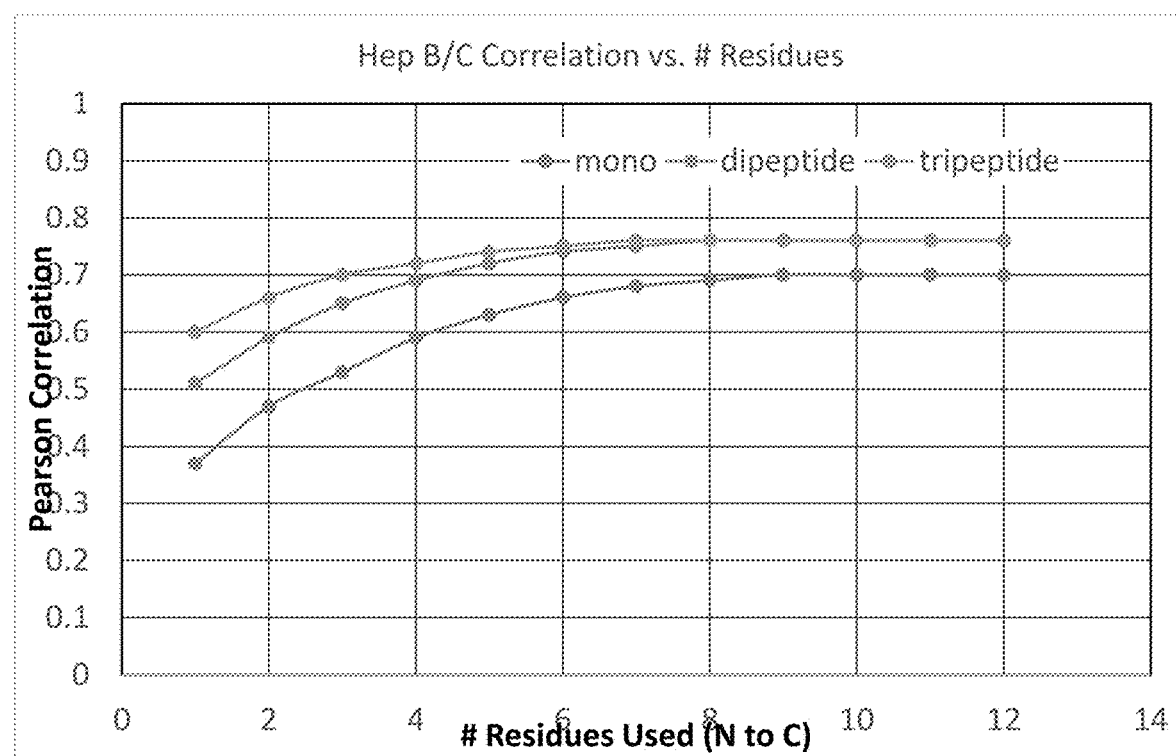
FIG. 18 shows correlation (model vs. data) with increasing number of residues in fitting one position at a time.

FIG. 18 shows correlation (model vs. data) with increasing number of residues in fitting one position at a time. The result for position by position fitting is generally similar, perhaps saturating slightly faster. As before, the tripeptides are overfit.

Figure 19:
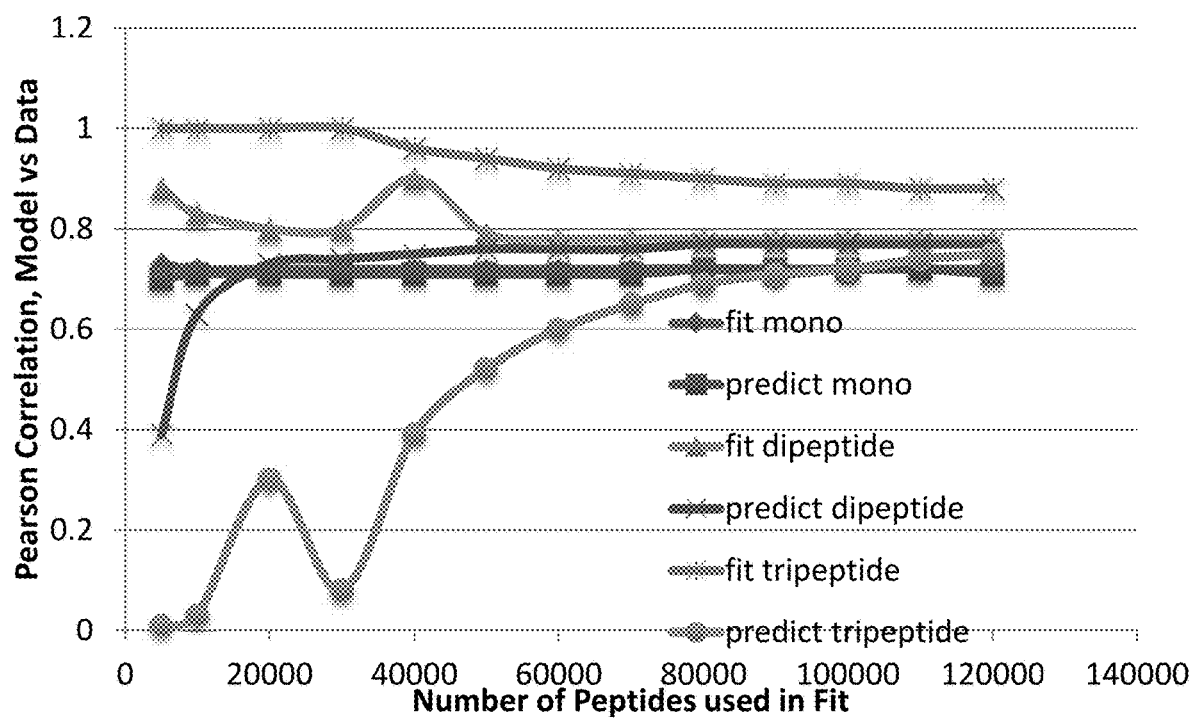
FIG. 19 shows correlation (model vs. data) with increasing number of peptides using full linear fit model.

FIG. 19 shows correlation (model vs. data) with increasing number of peptides using full linear fit model. Similar to the DM1A data, rapid saturation of mono-peptides and di-peptides, but tri-peptide never saturates. Further, performance likely will increase to ~0.8 with more peptides.

Figure 20:
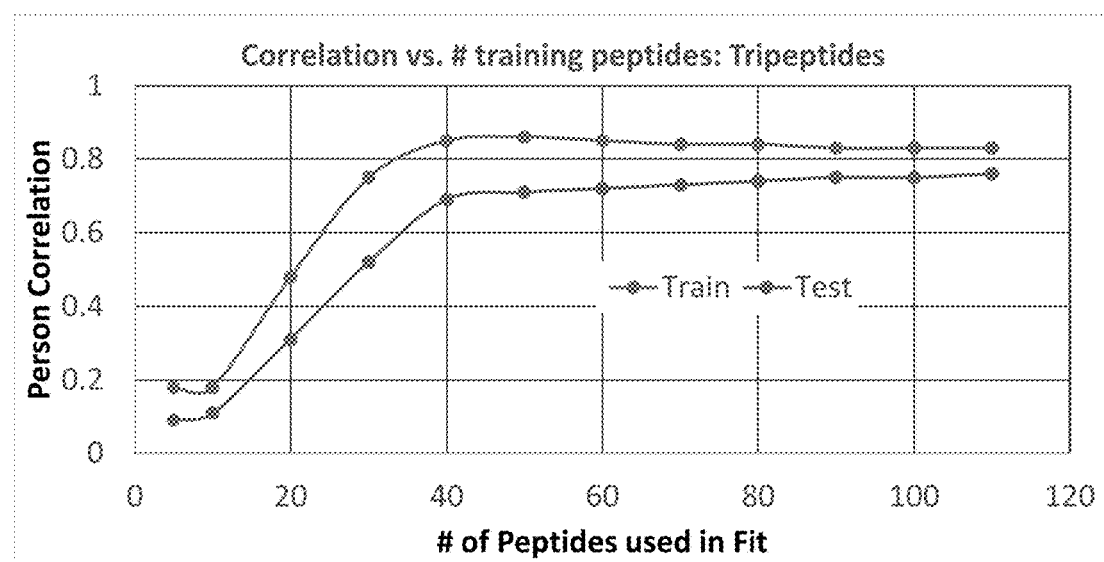
FIG. 20 shows correlation (model vs. data) with increasing number of peptides fitting one position at a time.

FIG. 20 shows correlation (model vs. data) with increasing number of peptides fitting one position at a time. With position by position fitting, the tri-peptide fit improves faster, but approaches about the same correlation. Again, more peptides would likely help. Mono-peptides and di-peptides are not much different from previous slide.

Overall, this examples shows that fraction of IgG information being captured depends on the model used (mono, di, tripeptide). For the best fits, it is approaching 60% based on $R^2$.

Example 5: Discrimination of Two Diseases

This example shows that the information captured in the predictive algorithms includes disease specific information. This example considers 44 Hepatitis B virus samples and 44 Hepatitis C virus samples. The model fits samples independently. The classification between Hepatitis B versus C is performed on various data sets: the original data, the data reconstructed from the fits, the original minus the reconstructed data, and the coefficients from the fit. Further, 4-fold cross validation is performed. The validation either uses the same peptides to fit and validate or generates parameters on one set of sequences and then use a complete different set to classify.

Table 6 shows classification results based on the recalculated data for the classification.

TABLE 6

| Dataset | AUC | |
| --- | --- | --- |
| | Data from fit | Original minus fit |
| Full med norm dataset | 0.78 | |
| Recalculated data from 1-mer fit | 0.63 | 0.73 |
| Recalculated data from 2-mer fit | 0.73 | 0.74 |
| Recalculated data from 3-mer fit | 0.75 | 0.75 |

Table 7 shows the results using the fitting coefficients as in the classification. By transforming the data via the fit, it is possible to train on one set of samples and half the peptides and distinguish diseases using that classifier applied to another set of samples and another set of peptides.

TABLE 7

| Dataset | AUC | |
| --- | --- | --- |
| | Coefficients from training set | Coefficients from test set |
| Full med norm dataset | 0.78 | |
| monopeptide model | 0.73 | 0.75 |
| dipeptide model | 0.78 | 0.72 |
| tripeptide model | 0.76 | 0.70 |

In general, the classification accuracies are between 0.70 and 0.75, demonstrating that it is feasible to capture disease information.

The embodiments shown and described herein are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of predicting binding on a peptide array, the method comprising:
    (a) contacting a defined array with a training sample containing one or more antibodies, wherein the peptide array comprises a plurality of peptides;
    (b) processing interactions between the plurality of peptides and the one or more antibodies from the training sample according to a data fitting model; and
    (c) applying the model to interactions between the plurality of peptides and a test sample to predict binding associated with one or more antibodies; and
    (d) redesigning the peptide array based on the predicted binding associated with the one or more antibodies to include array features associated with new binding interactions predicted by the predicted binding associated with the one or more antibodies,
    wherein the data fitting model comprises equation (1) or (2):

$$F_i = S_i * \Sigma_j a_j C_{i,j} \quad (1)$$

$$F_i = S_i + \Sigma_j a_j C_{i,j} \quad (2)$$

wherein
    $F_i$ is the signal of the $i^{th}$ peptide;
    $C_{i,j}$ is the composition of the $i^{th}$ peptide given by the j value;
    $a_j$ is a coefficient; and
    $S_i$ represents the part of the signal that is due to the sequence of amino acids beyond what is determined from the composition of amino acids.

2. The method of claim 1, wherein the data fitting model further comprises calculating $f_i$ according to equation 3, wherein an expression of formula (4) is minimized $$f_i = \Sigma_j a_j C_{i,j} \quad (3)$$

$$\Sigma_i (F_i - f_i)^2 \quad (4).$$

3. The method of claim 1, wherein said processing comprises imaging said interactions between the plurality of peptides and said antibodies.

4. The method of claim 3, wherein said interactions between the plurality of peptides and said antibodies are imaged by detecting a fluorescent marker associated with said antibodies.

5. The method of claim 1, wherein the processing is performed by a programmed digital processing device which comprises one or more non-transitory computer readable storage media encoded with one or more programs that processes information about interactions between the plurality of peptides and the one or more antibodies according to a data fitting model.

6. A method of characterizing one or more antibodies through interaction with one or more peptides on a peptide array, the method comprising:
   (a) contacting a defined peptide array having a plurality of peptides with a training sample containing one or more antibodies;
   (b) processing interactions between the plurality of peptides and the one or more antibodies from the training sample according to a data fitting model, wherein the data fitting model is a monopeptide fit, a dipeptide fit, or a tripeptide fit model;
   (c) applying the model to interactions between the plurality of peptides and a test sample to characterize one or more antibodies through the binding of said one or more antibodies and said plurality of peptides; and
   (d) redesigning the peptide array based on the characterizing of the one or more antibodies through the binding of said one or more antibodies and said plurality of peptides to improve array features of the peptide array for disease binding.

7. The method of claim 6, wherein said plurality of peptides are overlapping sequences of a proteome and said characterizing one or more antibodies comprises defining an antigen according to binding of one or more of said overlapping sequences of said proteome with an antibody in said test sample.

8. The method of claim 6, wherein said processing comprises imaging said interactions between the plurality of peptides and said antibodies.

9. The method of claim 8, wherein said interactions between the plurality of peptides and said antibodies are imaged by detecting a fluorescent marker associated with said antibodies.

10. The method of claim 6, wherein the processing is performed by a programmed digital processing device which comprises one or more non-transitory computer readable storage media encoded with one or more programs that processes information about interactions between the plurality of peptides and the one or more antibodies according to the data fitting model to generate a classifier.

11. A method of making a peptide array with one or more binding characteristics that are defined for a given application, the method comprising:
   (a) contacting a defined peptide array having a plurality of peptides with a training sample containing one or more antibodies for said given application;
   (b) processing interactions between the plurality of peptides and the one or more antibodies from the training sample according to a data fitting model, wherein the data fitting model is a monopeptide fit, a dipeptide fit, or a tripeptide fit model;
   (c) applying the model to interactions between the plurality of peptides and a test sample containing one or more antibodies to thereby define a binding characteristic associated with said one or more antibodies; and
   (d) making a peptide array with peptides for said given application based on said binding characteristic defined in step (c).

12. The method of claim 11, wherein said given application is epitope mapping of an antigen.

13. The method of claim 11, wherein said given application is distinguishing between two or more diseases through analysis of the molecular differences between patient samples.

14. The method of claim 11, wherein said processing comprises imaging said interactions between the plurality of peptides and said antibodies.

* * * * *